United States Patent
Yi et al.

(10) Patent No.: US 11,888,283 B2
(45) Date of Patent: Jan. 30, 2024

(54) LASER DEVICE FOR SKIN TREATMENT

(71) Applicant: JEISYS MEDICAL INC., Seoul (KR)

(72) Inventors: Won Ju Yi, Gwangmyeong-si (KR); Min Young Kim, Incheon (KR); Joo Hee Cho, Gunpo-si (KR); Myeong Wook Gu, Incheon (KR); Byoung Jin Ko, Incheon (KR); Seong Jun Kim, Gumi-si (KR); Dong Hwan Kang, Incheon (KR)

(73) Assignee: JEISYS MEDICAL INC., Seoul (KR)

( * ) Notice: Subject to any disclaimer, the term of this patent is extended or adjusted under 35 U.S.C. 154(b) by 724 days.

(21) Appl. No.: 17/047,686

(22) PCT Filed: Jan. 31, 2020

(86) PCT No.: PCT/KR2020/001468
§ 371 (c)(1),
(2) Date: Oct. 14, 2020

(87) PCT Pub. No.: WO2020/226266
PCT Pub. Date: Nov. 12, 2020

(65) Prior Publication Data
US 2021/0242657 A1 Aug. 5, 2021

(30) Foreign Application Priority Data

May 3, 2019 (KR) .......................... 10-2019-0052168
May 3, 2019 (KR) .......................... 10-2019-0084036

(51) Int. Cl.
*H01S 3/102* (2006.01)
*H01S 3/109* (2006.01)
(Continued)

(52) U.S. Cl.
CPC .......... *H01S 3/1024* (2013.01); *A61N 5/0616* (2013.01); *H01S 3/0941* (2013.01);
(Continued)

(58) Field of Classification Search
CPC ...... H01S 3/1024; H01S 3/0941; H01S 3/109; H01S 5/0428; H01S 3/10038;
(Continued)

(56) References Cited

U.S. PATENT DOCUMENTS 5,018,163 A * 5/1991 Daunt .................... H01S 3/2333
372/105
5,721,749 A * 2/1998 Holleman ............... H01S 3/117
372/75

(Continued)

FOREIGN PATENT DOCUMENTS

KR 10-0767622 B1 10/2007
KR 10-1575729 B1 12/2015
(Continued)

OTHER PUBLICATIONS

International Search Report for PCT/KR2020/001468 dated May 12, 2020 from Korean Intellectual Property Office.

*Primary Examiner* — Vu A Vu
(74) *Attorney, Agent, or Firm* — Revolution IP, PLLC

(57) ABSTRACT

A laser device for skin treatment includes: a laser generating unit including a diode laser for generating a pulse capable of being varied to a pulse width of 100 picoseconds (ps) to 2000 ps by a dedicated driver having a rising time of 100 ps or less and a pulse width adjustment unit for adjusting a width of the pulse generated by the diode laser, the laser generating unit configured to generate a single or a plurality of pulses; and a laser amplifying unit including a pumping lamp and a single or a plurality of amplification mediums having a rod structure for absorbing light energy from the pumping lamp, wherein, in the laser amplifying unit, a pulse supplied from the laser generating unit passes through at least one of the single or a plurality of amplification mediums a plurality of times inward from the outside and is gradually amplified.

11 Claims, 4 Drawing Sheets

(51) Int. Cl.
  *H01S 3/0941* (2006.01)
  *A61N 5/06* (2006.01)
  *A61B 17/00* (2006.01)
  *A61N 5/067* (2006.01)

(52) U.S. Cl.
  CPC ...... *H01S 3/109* (2013.01); *A61B 2017/0019* (2013.01); *A61N 5/067* (2021.08); *A61N 2005/0666* (2013.01)

(58) Field of Classification Search
  CPC ...... H01S 3/0092; H01S 3/092; H01S 3/2333; H01S 3/2316; A61N 5/0616; A61N 5/067; A61N 2005/0666; A61N 2005/0626; A61N 2005/0632; A61B 2017/0019; A61B 2017/00747; A61B 18/203
  USPC .......................................................... 372/25
  See application file for complete search history.

(56) References Cited

U.S. PATENT DOCUMENTS

| | | | | |
|---|---|---|---|---|
| 5,742,634 A | * | 4/1998 | Rieger | H01S 3/2341 |
| | | | | 372/13 |
| 6,580,732 B1 | * | 6/2003 | Guch, Jr. | H01S 3/1103 |
| | | | | 372/71 |
| 7,418,022 B2 | * | 8/2008 | Govorkov | H01S 3/10092 |
| | | | | 372/55 |
| 7,620,092 B2 | * | 11/2009 | Wang | H01S 3/2316 |
| | | | | 372/101 |
| 8,170,078 B2 | * | 5/2012 | Ershov | H01S 3/225 |
| | | | | 372/57 |
| 8,995,482 B1 | * | 3/2015 | Moshchansky-Livingston | |
| | | | | H01S 3/10092 |
| | | | | 372/98 |
| 9,008,144 B2 | * | 4/2015 | Pang | H01S 3/1673 |
| | | | | 372/100 |
| 9,190,798 B2 | * | 11/2015 | Caprara | H01S 3/0092 |
| 9,590,386 B2 | * | 3/2017 | Harter | H01S 3/094003 |
| 9,993,159 B2 | * | 6/2018 | Islam | A61B 5/0091 |
| 2016/0135891 A1 | * | 5/2016 | Feldman | A61B 18/20 |
| | | | | 606/3 |
| 2017/0063019 A1 | | 3/2017 | Yu et al. | |
| 2017/0184942 A1 | | 6/2017 | Clark et al. | |

FOREIGN PATENT DOCUMENTS

| | | |
|---|---|---|
| KR | 10-1898632 B1 | 9/2018 |
| KR | 10-2018-0120137 A | 11/2018 |
| KR | 10-1915750 B1 | 11/2018 |
| KR | 10-1915757 B1 | 11/2018 |

* cited by examiner

LASER DEVICE FOR SKIN TREATMENT

TECHNICAL FIELD

The present invention relates to a laser device for skin treatment, and more particularly, to a laser device for skin treatment including a laser generating unit in which pulse width adjustment can be easily performed.

BACKGROUND ART

Recently, research on a field using lasers is being actively conducted in the industry and research sites. In particular, these lasers have recently been briskly developed in research fields such as spectroscopy, nano-imaging, particle acceleration, and nuclear fusion, as well as life sites such as three-dimensional (3D) printing, roughening, and communication performances, and industrial sites such as welding, cutting, and surface modification.

Accordingly, various types of laser generating devices and laser amplifying devices have been developed. However, laser generating devices and laser amplifying devices according to the related art have a problem in that the structure becomes complicated in order to obtain various types of pulse waves and when the structure is simplified, output decreases.

DETAILED DESCRIPTION OF THE INVENTION

Technical Problem

The present invention provides a laser device for skin treatment including a laser generating unit in which pulse width adjustment can be easily performed.

Technical Solution

According to an aspect of the present invention, there is provided a laser device for skin treatment, including a laser generating unit including a diode laser for generating a pulse capable of being varied to a pulse width of 100 picoseconds (ps) to 2000 ps by a dedicated driver having a rising time of 100 ps or less and a pulse width adjustment unit for adjusting a width of the pulse generated by the diode laser, the laser generating unit configured to generate a single or a plurality of pulses, and a laser amplifying unit including a pumping lamp and a single or a plurality of amplification mediums having a rod structure for absorbing light energy from the pumping lamp, wherein, in the laser amplifying unit, a pulse supplied from the laser generating unit may pass through at least one of the single or a plurality of amplification mediums a plurality of times inward from the outside and may be gradually amplified.

According to another aspect of the present invention, there is provided a laser device for skin treatment, including a laser generating unit including a diode laser for generating a pulse and a pulse width adjustment unit for adjusting a width of the pulse generated by the diode laser, the laser generating unit configured to generate a single or a plurality of pulses, and a laser amplifying unit including a pumping lamp and an amplification medium for absorbing light energy from the pumping lamp, wherein, in the laser amplifying unit, a pulse supplied from the laser generating unit may pass through the amplification medium a plurality of times and may be gradually amplified.

According to another aspect of the present invention, there is provided a laser device for skin treatment, including a laser generating unit generating a pulse having an adjusted pulse width and a laser amplifying unit amplifying the pulse supplied from the laser generating unit, wherein the laser amplifying unit includes a first amplification medium for first amplifying the pulse supplied from the laser generating unit, and a first mirror arranged to reflect the laser pulse first amplified while passing through the first amplification medium and to return the first amplified laser pulse in a direction of the first amplification medium, a first beam splitter arranged to face the first mirror with the first amplification medium therebetween and to adjust a path of the pulse second amplified while returning to and passing through the first amplification medium, a first wave plate arranged between the first mirror and the first beam splitter to change a polarization or phase of the passing pulse, a second mirror transmitting the pulse having the path adjusted by the first beam splitter to a second amplification medium, the second amplification medium spaced apart from the first amplification medium and for third amplifying the pulse supplied from the second mirror, a first pumping lamp spaced apart from the first amplification medium and the second amplification medium and illuminating the first amplification medium and the second amplification medium, a third mirror arranged to face the second mirror with the second amplification medium therebetween, to reflect the pulse third amplified while passing through the second amplification medium and to adjust a path of the third amplified pulse, a fourth mirror transmitting the pulse having the path adjusted by the third mirror to a third amplification medium, a third amplification medium for fourth amplifying the pulse supplied from the fourth mirror, a fifth mirror arranged to face the fourth mirror with the third amplification medium therebetween, to reflect the pulse fourth amplified while passing through the third amplification medium and to adjust a path of the fourth amplified pulse, a sixth mirror transmitting the pulse having the path adjusted by the fifth mirror to a fourth amplification medium, a fourth amplification medium for fifth amplifying the pulse supplied from the sixth mirror, a second pumping lamp spaced apart from the third amplification medium and the fourth amplification medium and illuminating the third amplification medium and the fourth amplification medium, and a seventh mirror arranged to face the sixth mirror with the fourth amplification medium therebetween, to reflect the pulse passing through the fourth amplification medium and to adjust a path of the pulse, and wherein the pulse supplied from the laser generating unit may transmit the first beam splitter and may be directed to the first amplification medium.

According to another aspect of the present invention, there is provided a laser device for skin treatment, including a laser generating unit generating a pulse having an adjusted pulse width and a laser amplifying unit amplifying the pulse supplied from the laser generating unit, wherein the laser amplifying unit includes a first amplification medium for first amplifying the pulse supplied from the laser generating unit, a first mirror arranged to reflect the laser pulse first amplified while passing through the first amplification medium and to return the first amplified laser pulse in a direction of the first amplification medium, a first beam splitter arranged to face the first mirror with the first amplification medium therebetween and to adjust a path of the pulse second amplified while returning to and passing through the first amplification medium, a first wave plate arranged between the first mirror and the first beam splitter to change a polarization or phase of the passing pulse, a second mirror transmitting the pulse having the path adjusted by the first beam splitter to a second amplification medium, the second amplification medium spaced apart from the first amplification medium and for third amplifying the pulse supplied from the second mirror, a first pumping lamp spaced apart from the first amplification medium and the second amplification medium and illuminating the first amplification medium and the second amplification medium, a third mirror arranged to reflect the pulse third amplified while passing through the second amplification medium and to return the third amplified pulse in a direction of the second amplification medium, a second beam splitter arranged to face the third mirror with the second amplification medium therebetween and to adjust a path of the pulse fourth amplified while returning to and passing through the second amplification medium, a third wave plate arranged between the third mirror and the second beam splitter to change a polarization or phase of the passing pulse, and a second wave plate in which the pulse reflected from the second mirror is supplied to the second amplification medium through the second beam splitter and which is arranged between the second mirror and the second beam splitter and changing a polarization or phase of the pulse reflected from the second mirror and directed to the second beam splitter, and wherein the pulse supplied from the laser generating unit may transmit the first beam splitter and may be directed to the first amplification medium.

According to another aspect of the present invention, there is provided a laser device for skin treatment, including a laser generating unit generating a pulse having an adjusted pulse width and a laser amplifying unit amplifying the pulse supplied from the laser generating unit, wherein the laser amplifying unit includes a first amplification medium for first amplifying the pulse supplied from the laser generating unit, a first mirror adjusting a path of the pulse first amplified while passing through the first amplification medium, a second mirror transmitting the pulse having the path adjusted by the first mirror to a second amplification medium, the second amplification medium spaced apart from the first amplification medium and for second amplifying the pulse supplied from the second mirror, a first pumping lamp spaced apart from the first amplification medium and the second amplification medium and illuminating the first amplification medium and the second amplification medium, a second beam splitter allowing the second amplified pulse by the second amplification medium to pass, a third mirror arranged to face the second amplification medium with the second beam splitter therebetween, to reflect the pulse second amplified while passing through the second amplification medium and passing through the second beam splitter and to adjust a path of the pulse, a first wave plate arranged between the third mirror and the second beam splitter to change a polarization or phase of the pulse passing through the second beam splitter and directed to the third mirror, a first beam splitter arranged to face the first mirror with the first amplification medium therebetween, to reflect the pulse having the path adjusted by the third mirror and to adjust a path of the pulse, wherein the pulse having the path adjusted by the first beam splitter may be third amplified while passing the first amplification medium, the third amplified pulse may be directed to the second mirror while the path of the third amplified pulse is adjusted by the first mirror, the pulse having the path adjusted by the second mirror may be directed to the second amplification medium, and the fourth amplified pulse while passing through the second amplification medium may be sent out while the path of the fourth amplified pulse is adjusted by the second beam splitter, and the pulse supplied from the laser generating unit may transmit the first beam splitter and may be directed to the first amplification medium.

Effects of the Invention

A laser device for skin treatment according to the present invention has the following effects.

Firstly, not only the width of a pulse generated by a laser generating unit can be conveniently adjusted, but also the pulse can be easily amplified by a laser amplifying unit.

Secondly, the width of the pulse can be easily adjusted so that various types of pulse waves can be easily generated.

Thirdly, since on/off control using a diode laser is used, it is easy to operate.

Fourthly, since the laser amplifying unit can amplify and output the pulse, pulses having various pulse wavelengths, pulse widths, and energy can be continuously or discontinuously output to a skin treatment subject. In particular, the structure of the laser amplifying unit is very simple so that it is easy to amplify the pulse.

MODE OF THE INVENTION

Hereinafter, exemplary embodiments of the present invention will be described with reference to the accompanying drawings.

Figure 1:
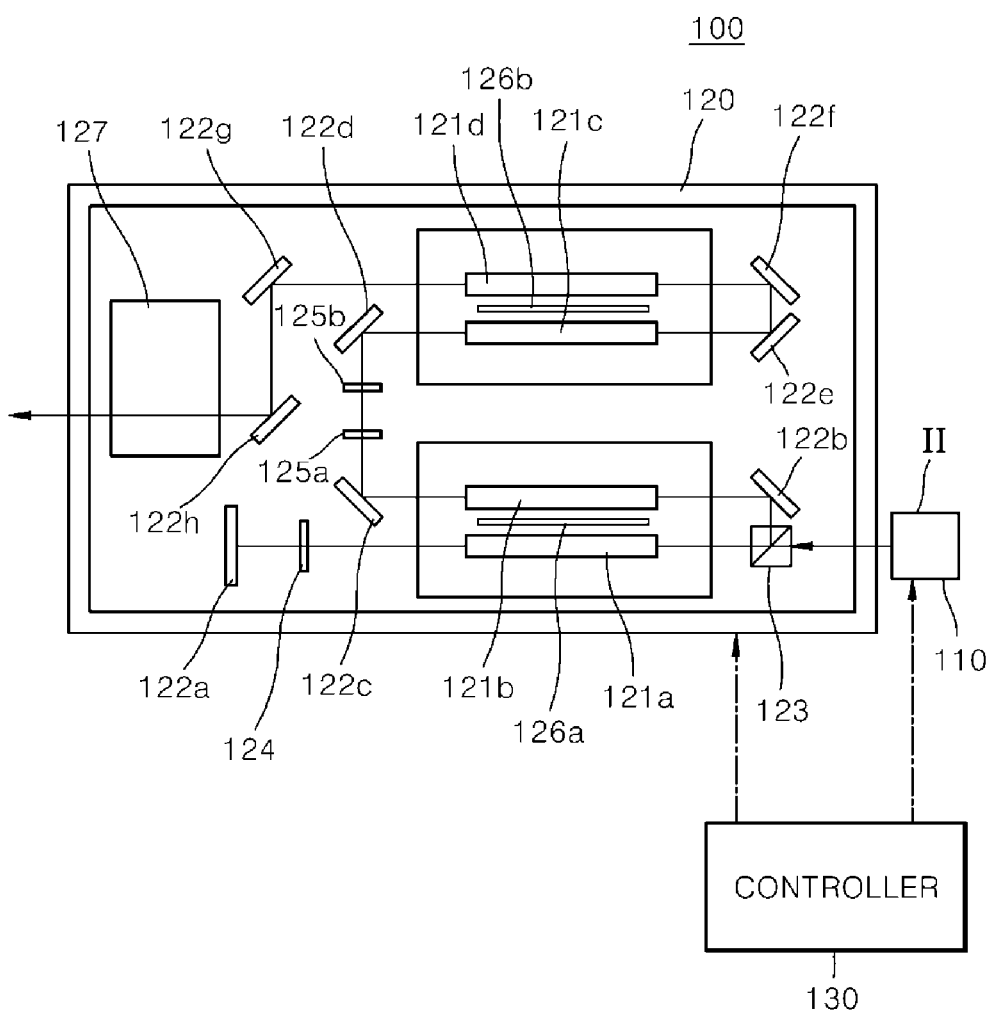
FIG. 1 is a schematic diagram of a laser device for skin treatment according to an embodiment of the present invention.
Figure 2:
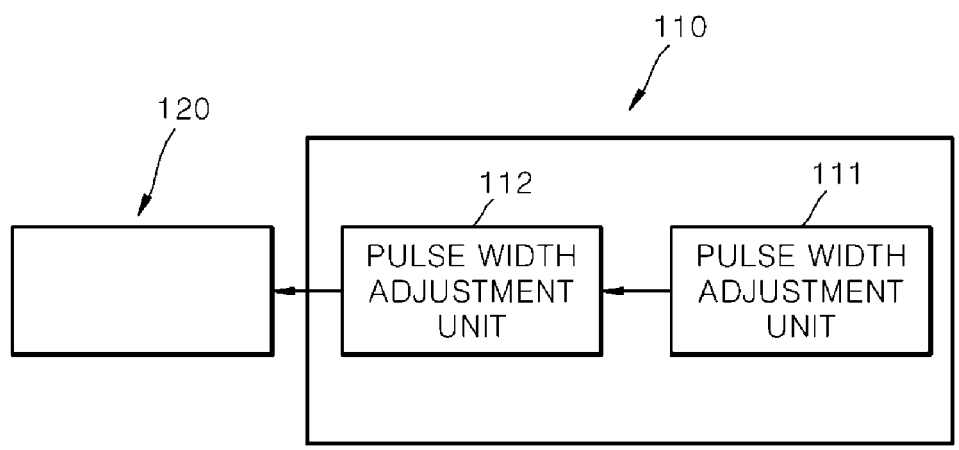
FIG. 2 is a block diagram illustrating the configuration of a laser generating unit of the laser device for skin treatment shown in FIG. 1.

Referring to FIGS. 1 and 2, a laser device for skin treatment 100 according to an embodiment of the present invention includes a laser generating unit 110, a laser amplifying unit 120, and a controller 130. The laser generating unit 110 includes a laser source generating unit 111 and a pulse width adjustment unit 112.

The laser source generating unit 111 emits a seed laser. The laser source generating unit 111 is formed as a laser diode having a wavelength of 1064 nm. The laser source generating unit 111 generates a laser pulse through on/off control. A pulse generated by the laser source generating unit 111 may be varied in a pulse width of 100 picoseconds (ps) to tens of milliseconds (ms). The width of the laser pulse generated by the laser source generating unit 111 may be varied by the pulse width adjustment unit 112 in real time according to an input signal of the controller 130. Also, the pulse generated by the laser source generating unit 111 is formed as a P-wave. The laser source generating unit 111 may generate a single or a plurality of laser pulses. However, the present invention is not limited thereto, and the laser source generating unit 111 may be changed to another type.

The pulse width adjustment unit 112 adjusts energy, a pulse width, and the number of pulses of a laser source generated by the laser source generating unit 111 to generate a plurality of modulated laser source having different energies, pulse widths and number of pulses. The adjustment of the pulse width adjustment unit 112 is performed according to a signal of the controller 130. The pulse width adjustment unit 112 includes a dedicated driver. Since the dedicated driver of the diode laser has a short rising time of 100 ps or less, a pulse width control of several hundreds of ps is used. In the case of the dedicated driver of the diode laser, a driver for short pulses of ps or a driver for controlling pulses of ms or more may be selected and used.

The pulse width adjustment unit 112 sends out any one of the plurality of modulated laser sources or any one of the laser sources generated by the laser source generating unit 111 to the laser amplifying unit 120. Of course, the pulse width adjustment unit 112 may alternately send out any one of the plurality of modulated laser sources and the laser sources generated by the laser source generating unit 111 to the laser amplifying unit 120. Also, the pulse width adjustment unit 112 may alternately send out the plurality of modulated laser sources and the laser sources generated by the laser source generating unit 111 to the laser amplifying unit 120 or may alternately send out the plurality of modulated laser sources to the laser amplifying unit. The laser generating unit 120 may vary the pulse width in real time according to the input signal of the controller 130. Thus, laser pulses having various pulse widths can be easily generated.

The laser amplifying unit 120 includes a first beam splitter 123, a first amplification medium 121a, a first mirror 122a, a first wave plate 124, a second mirror 122b, a second amplification medium 121b, a third mirror 122c, a fourth mirror 122d, a third amplification medium 121c, a fifth mirror 122e, a sixth mirror 122f, a fourth amplification medium 121d, a seventh mirror 122g, an eighth mirror 122h, a first lens 125a, a second lens 125b, a first pumping lamp 126a, a second pumping lamp 126b, and a second harmonic generator (SHG) 127. The first beam splitter 123 transmits p-polarization and reflects S-polarization. Thus, since the laser pulse supplied from the laser generating unit 110 is a P-wave, it transmits the first beam splitter 123 as it is. Also, the first beam splitter 123 is arranged on the same axis as a proceeding direction of the laser source supplied from the laser generating unit 110. Of course, the arrangement of the first beam splitter 123 may be changed. Another role of the first beam splitter 123 will be described later.

The first amplification medium 121a serves to amplify the laser source supplied from the laser generating unit 110 while passing through a single or multiple times. The first pumping lamp 126a illuminates the first amplification medium 121a so as to excite ions in the first amplification medium 121a. The first pumping lamp 126a is spaced apart from the first amplification medium 121a. The first amplification medium 121a is formed in a rod structure. Also, the firsts amplification medium 121a is formed of Nd:YAG. However, in the present invention, the structure and shape of the first amplification medium 121a may be changed as much as possible.

Also, the first amplification medium 121a is arranged on the same axis as the first beam splitter 123. Thus, the laser pulse that transmits the first beam splitter 123 is first amplified while passing through the first amplification medium 121a.

The first mirror 122a is arranged on the same axis as the first beam splitter 123 and the first amplification medium 121a. Thus, the first mirror 122a is a total reflection mirror that reflects the laser pulse first amplified while passing through the first amplification medium 121a in a direction of the first amplification medium 121a. The first mirror 122a serves to return the first amplified laser pulse while passing through the first amplification medium 121a to amplify it once again by the first amplification medium 121a.

In this case, the first wave plate 124 is arranged between the first amplification medium 121a and the first mirror 122a. The first wave plate 124 is formed as a quarter-waveplate (QWP) that changes the phase of a wave passing through the first wave plate 124 by ¼ wavelength. That is, the first wave plate 122c changes the phase of the laser pulse directed to the first mirror 122a by passing through the first amplification medium 121a by ¼ wavelength and changes the phase of the laser pulse reflected from the first mirror 122a and returning to the first amplification medium 121a by ¼ wavelength again. Thus, the p-wave supplied from the laser generating unit 110 passes through the first wave plate 124 twice and is changed into an s-wave. This is to change the proceeding path of the laser pulse by reflecting rather than transmitting when returning to the first beam splitter 123.

The laser pulse that returns to the first amplification medium 121a again after passing the first wave plate 124 twice passes through the first amplification medium 121a and is second amplified. The path of the second amplified laser pulse is adjusted by the first beam splitter 123. That is, the second amplified laser pulse is reflected by the first beam splitter 123, and the path of the second amplified laser pulse is changed by 90 degrees.

The second mirror 122b is formed above the first beam splitter 123. Thus, the laser pulse reflected by the first beam splitter 123 is reflected from the second mirror 122b. The second mirror 122b is arranged in such a way that the laser pulse supplied from the first beam splitter 123 may be reflected in a direction of the second amplification medium 121b.

The second amplification medium 121b serves to third amplify the laser pulse reflected from the second mirror 122b. The second amplification medium 121b is spaced apart from the first amplification medium 121a. Ions in the second amplification medium 121b may be excited by the first pumping lamp 126b. The second amplification medium 121b is formed in a rod structure. The second amplification medium 121a is formed of Nd:YAG. However, in the present invention, the structure and shape of the second amplification medium 121b may be changed as much as possible.

Also, the second amplification medium 121b is arranged above the first amplification medium 121a. Also, the second amplification medium 121b is arranged on the same axis as the second mirror 122b. That is, the second amplification medium 121b may also be arranged below the first amplification medium 121a according to the arrangement location of the second mirror 122b.

The third mirror 122c is arranged to face the second mirror 122b with the second amplification medium 121b therebetween. The third mirror 122c reflects the third amplified laser pulse while passing through the second amplification medium 121b and adjusts the path of the third amplified laser pulse. That is, the third mirror 122c serves to reflect the laser pulse passing through the second amplification medium 121b so that the path of the laser pulse may be changed by 90 degrees. Of course, the reflection angle of the laser pulse reflected from the third mirror 122c may be changed. The third mirror 122c is also arranged on the same axis as the second mirror 122b and the second amplification medium 121b.

The fourth mirror 122d reflects the laser pulse supplied from the third mirror 122c in a direction of the third amplification medium 121c. In this case, the proceeding path of the laser pulse directed to the fourth mirror 122d from the third mirror 122c may further include lens units 125a and 125b for adjusting the spatial size of the laser pulse. The lens units 125a and 125b may include a first lens 125a and a second lens 125b. The lens units 125a and 125b may adjust a distance between the first lens 125a and the second lens 125b to adjust the spatial size of the laser pulse directed to the fourth mirror 122d from the third mirror 122c.

The third amplification medium 121c serves to fourth amplify the laser pulse reflected from the fourth mirror 122b. The third amplification medium 121c is spaced apart from the fourth amplification medium 121d. Ions in the third amplification medium 121c may be excited by the second pumping lamp 126b. The third amplification medium 121c is formed in a rod structure. The third amplification medium 121c is formed of Nd:YAG. However, in the present invention, the structure and shape of the third amplification medium 121c may be changed as much as possible.

The fifth mirror 122e is arranged to face the fourth mirror 125b with the third amplification medium 121c therebetween. The fifth mirror 122e reflects the fourth amplified laser pulse while passing through the third amplification medium 121c and adjusts the path of the fourth amplified laser pulse. That is, the fifth mirror 122e serves to reflect the laser pulse passing through the third amplification medium 121c to change the path of the laser pulse by 90 degrees. Of course, the reflection angle of the laser pulse reflected from the fifth mirror 122e may be changed. The fifth mirror 122e is arranged on the same axis as the fourth mirror 122d and the third amplification medium 121c.

The sixth mirror 122f reflects the laser pulse supplied from the fifth mirror 122e in a direction of the fourth amplification medium 121d. In the present embodiment, the sixth mirror 122f is formed separately from the fifth mirror 122e, but the fifth mirror 122e and the sixth mirror 122f may be formed as one mirror.

The fourth amplification medium 121d serves to fifth amplify the laser pulse reflected from the sixth mirror 122f. The fourth amplification medium 121d is spaced apart from the third amplification medium 121c. Ions in the fourth amplification medium 121d may be excited by the second pumping lamp 126d. The fourth amplification medium 121d is formed in a rod structure. The fourth amplification medium 121d is formed of Nd:YAG. However, in the present invention, the structure and shape of the fourth amplification medium 121d may be changed as much as possible.

The seventh mirror 122g is arranged to face the sixth mirror 122f with the fourth amplification medium 121d therebetween. Also, the seventh mirror 122g reflects the laser pulse passing through the fourth amplification medium 121d to adjust the path of the laser pulse in a direction of the eighth mirror 122h.

The eighth mirror 122h is arranged on one side of the seventh mirror 122g and adjusts the path of the laser pulse supplied from the seventh mirror 122g. The laser pulse having the path adjusted by the eighth mirror 122h is output to the laser amplifying unit 120. However, the present invention is not limited thereto, and the laser pulse may be output to the laser amplifying unit 120 directly from the seventh mirror 122g.

The SHG 127 changes the wavelength of the laser pulse output from the seventh mirror 122g or the eighth mirror 122h. The SHG 127 is arranged on a path on which the laser pulse output from the seventh mirror 122g or the eighth mirror 122h proceeds. The SHG 127 changes the wavelength of the laser pulse output from the eighth mirror 122h similarly to a known wavelength-changing method.

The controller 130 serves to control the laser generating unit 110 and the laser amplifying unit 120. That is, the controller 130 adjusts energy and a pulse width of the laser source generated by applying a signal to the laser source generating unit 111 and the pulse width adjustment unit 112. At this time, the controller 130 varies the pulse width by using the dedicated driver of the diode laser included in the laser generating unit 110. Since the dedicated driver of the diode laser has a short rising time of 100 ps or less, a pulse width control of several tens of ps is used. In the case of the dedicated driver of the diode laser, a driver for short pulses of ps or a driver for controlling pulses of ms or more may be selected and used.

Also, the controller 130 may control the states of the first amplification medium 121a, the second amplification medium 121b, the third amplification medium 121c, and the fourth amplification medium 121d by applying signals to the first pumping lamp 126a and the second pumping lamp 126b of the laser amplifying unit 120. Also, the controller 130 may also control the laser pulse generated by transmitting the signal to the laser generating unit 110 when the laser pulse output by the laser amplifying unit 120 does not have a required energy level.

The laser device for skin treatment 100 according to the present embodiment has a structure in which the pulse width can be conveniently varied by the laser generating unit 110 and the laser pulse generated by the laser generating unit 110 can be repeatedly amplified several times, so that the laser pulse with small energy generated by the laser generating unit 110 can be amplified to a laser pulse with large energy.

In FIG. 1, one first pumping lamp 126a and one second pumping lamp 126b are arranged. However, the present invention is not limited thereto. Each of the first pumping lamp 126a and the second pumping lamp 126b has a structure including two lamps so that each lamp of the first pumping lamp 126a irradiates light to the first amplification medium 121a and the second amplification medium 121b and each of the second pumping lamp 126b irradiates light to the third amplification medium 121c and the fourth amplification medium 121d. In this case, the laser amplifying unit 120 can be easily controlled.

Figure 3:
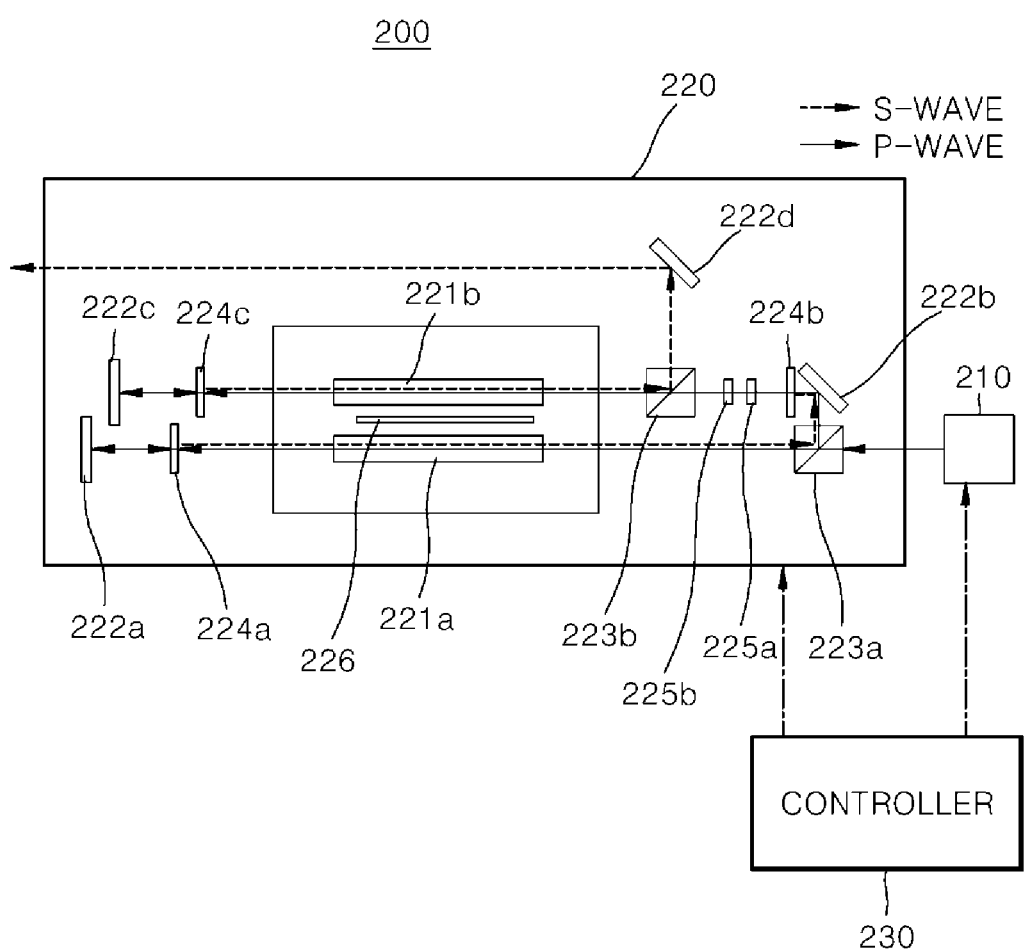
FIG. 3 is a schematic diagram of a laser device for skin treatment according to another embodiment of the present invention.

Referring to FIG. 3, a laser device for skin treatment 200 according to another embodiment of the present invention includes a laser generating unit 210, a laser amplifying unit 220, and a controller 230. Also, the laser generating unit 210 may include a laser source generating unit (not shown) and a pulse width adjustment unit (not shown), as in the laser generating unit 110 shown in FIG. 1. In the laser device for skin treatment 200 according to the present embodiment, the laser generating unit 210 and the controller 230 are similar to the laser device for skin treatment 100 of FIG. 1 and thus, a description thereof will be omitted.

The laser amplifying unit 220 includes a first beam splitter 223a, a first amplification medium 221a, a first mirror 222a, a first wave plate 224a, a second mirror 222b, a second wave plate 224b, a second amplification medium 221b, a first pumping lamp 226, a third mirror 222c, a second beam splitter 223b, a third wave plate 224c, a first lens 225a, a second lens 225b, and a fourth mirror 222d. Although not shown, an SHG (not shown) as in FIG. 1 may be further included in the laser amplifying unit 220. The first beam splitter 223a transmits P-polarized light and reflects S-polarized light. Thus, the laser pulse supplied from the laser generating unit 210 is a P-wave as in the laser generating unit 110 shown in FIG. 1 and thus transmits the first beam splitter 223a as it is. Also, the first beam splitter 223a is arranged on the same axis as the proceeding direction of the laser source supplied from the laser generating unit 210. Of course, the arrangement of the first beam splitter 223a may be changed.

The first amplification medium 221a serves to amplify the laser source supplied from the laser generating unit 210. The first pumping lamp 226 illuminates the first amplification medium 221a so as to excite ions in the first amplification medium 221a. The first pumping lamp 226a is spaced apart from the first amplification medium 221a. The first amplification medium 221a is formed in a rod structure. The first amplification medium 221a is formed of Nd:YAG. However, in the present invention, the structure and shape of the first amplification medium 221a may be changed as much as possible.

Also, the first amplification medium 221a is arranged on the same axis as the first beam splitter 223a. Thus, the laser pulse that transmits the first beam splitter 223a is first amplified while passing through the first amplification medium 221a.

The first mirror 222a is arranged on the same axis as the first beam splitter 223a and the first amplification medium 221a. Also, the first mirror 222a is arranged to face the first beam splitter 223a with the first amplification medium 221a therebetween. The first mirror 222a is a total reflection mirror that reflects the laser pulse first amplified while passing through the first amplification medium 221a in a direction of the first amplification medium 221a. The first mirror 222a serves to return the first amplified laser pulse while passing through the first amplification medium 221a to amplify it once again by the first amplification medium 121a.

At this time, the first wave plate 224a is arranged between the first amplification medium 221a and the first mirror 222a. The first wave plate 224a is formed as a QWP that changes the phase of a wave passing through the first wave plate 224a by ¼ wavelength. After passing through the first amplification medium 221a, the laser pulse directed to the first mirror 222a by passing through the first wave plate 224a and the laser pulse reflected from the first mirror 222a and directed to the first wave plate 224a are circularly polarized and proceed. That is, the first wave plate 224a changes the phase of the laser pulse directed to the first mirror 222a by passing through the first amplification medium 221a by ¼ wavelength and changes the phase of the laser pulse reflected from the first mirror 222a and returning to the first amplification medium 221a by ¼ wavelength again. Thus, the p-wave supplied from the laser generating unit 210 passes through the first wave plate 224a twice and is changed into an S-wave. This is to change the proceeding path of the laser pulse by reflecting rather than transmitting when returning to the first beam splitter 223a.

The laser pulse that returns to the first amplification medium 221a again after passing through the first wave plate 224a twice is second amplified while passing through the first amplification medium 221a. The path of the second amplified laser pulse is adjusted by the first beam splitter 223a. That is, the second amplified laser pulse is reflected by the first beam splitter 223a, and the path of the second amplified laser pulse is changed by 90 degrees.

The second mirror 222b is arranged on one side in which the path of the first beam splitter 223a is changed by 90 degrees. Thus, the laser pulse reflected by the first beam splitter 223a is reflected from the second mirror 222b. The second mirror 222b is arranged in such a way that the laser pulse supplied from the first beam splitter 223a may be reflected in a direction of the second amplification medium 221b.

The second wave plate 224b changes the phase of the laser pulse that is reflected from the second mirror 222b and directed to the second amplification medium 221b. At this time, the second wave plate 224b is formed as a half wave plate (HWP), unlike in the first wave plate 224a. That is, the laser pulse supplied to the second wave plate 224b is an S-wave, and the laser pulse that passes through the second wave plate 224b changes the phase of the wave by ½ wavelength, resulting in a P-wave. This is to allow the laser pulse reflected from the second mirror 224b to transmit the second beam splitter 223b located to face the second mirror 224b with the second wave plate 224b therebetween.

The second beam splitter 223b is arranged between the second wave plate 224b and the second amplification medium 221b. Since the laser pulse passing through the second wave plate 224b is a P-wave, the second beam splitter 223b transmits the laser pulse rather than reflects it.

The first lens 225a and the second lens 225b are arranged between the second beam splitter 223b and the second wave plate 224b. The first lens 225a and the second lens 225b adjust the spatial size of the laser pulse reflected from the second mirror 222b.

The second amplification medium 221b serves to third amplify the laser source supplied by passing through the second beam splitter 223b. The first pumping lamp 226 illuminates the second amplification medium 221b so as to excite ions in the second amplification medium 221b. The first pumping lamp 226 is spaced apart from the second amplification medium 221b. The second amplification medium 221b is formed as a rod structure. The second amplification medium 221b is formed of Nd:YAG. However, in the present invention, the structure and shape of the second amplification medium 221b may be changed as much as possible.

The third mirror 222c serves to return to the second amplification medium 221b by reflecting the third amplified laser pulse while passing through the second amplification medium 221b. At this time, the third wave plate 224c is arranged between the third mirror 222c and the second amplification material 221b. The third wave plate 224c is formed as a QWP, as in the first wave plate 224a. Thus, the phase of the laser pulse is changed by ¼ wavelength while the laser pulse proceeds to the third mirror 222c from the second amplification medium 221b, and when returning to the second amplification medium 221b from the third mirror 222c, the phase of the laser pulse is changed by ¼ wavelength. After passing through the second amplification medium 221b, the laser 1o pulse directed to the third mirror 222c while passing through the third wave plate 224c and the laser pulse reflected from the third mirror 222c and directed to the third wave plate 224c are circularly polarized and proceed. That is, the waveform of the laser pulse returning to the second amplification medium 221b is changed from the P-wave to the S-wave.

The second beam splitter 223b reflects the laser pulse that is reflected from the third mirror 222c and is fourth amplified by passing through the second amplification medium 221b, to adjust the path of the laser pulse. The laser pulse having the path adjusted by being reflected by the second beam splitter 223b, is reflected by the fourth mirror 222d arranged on one side of the second beam splitter 223b and is output.

The laser device for skin treatment 200 according to the present embodiment has an advantage of having a simpler structure than the laser device for skin treatment 100 of FIG. 1, although the number of amplification times is four times that is less once compared to the laser device for skin treatment 100 of FIG. 1. Also, since there are four amplifications, it is possible to amplify low energy laser pulse generated by the laser generating unit 210 into a laser pulse having a sufficiently large energy.

Figure 4:
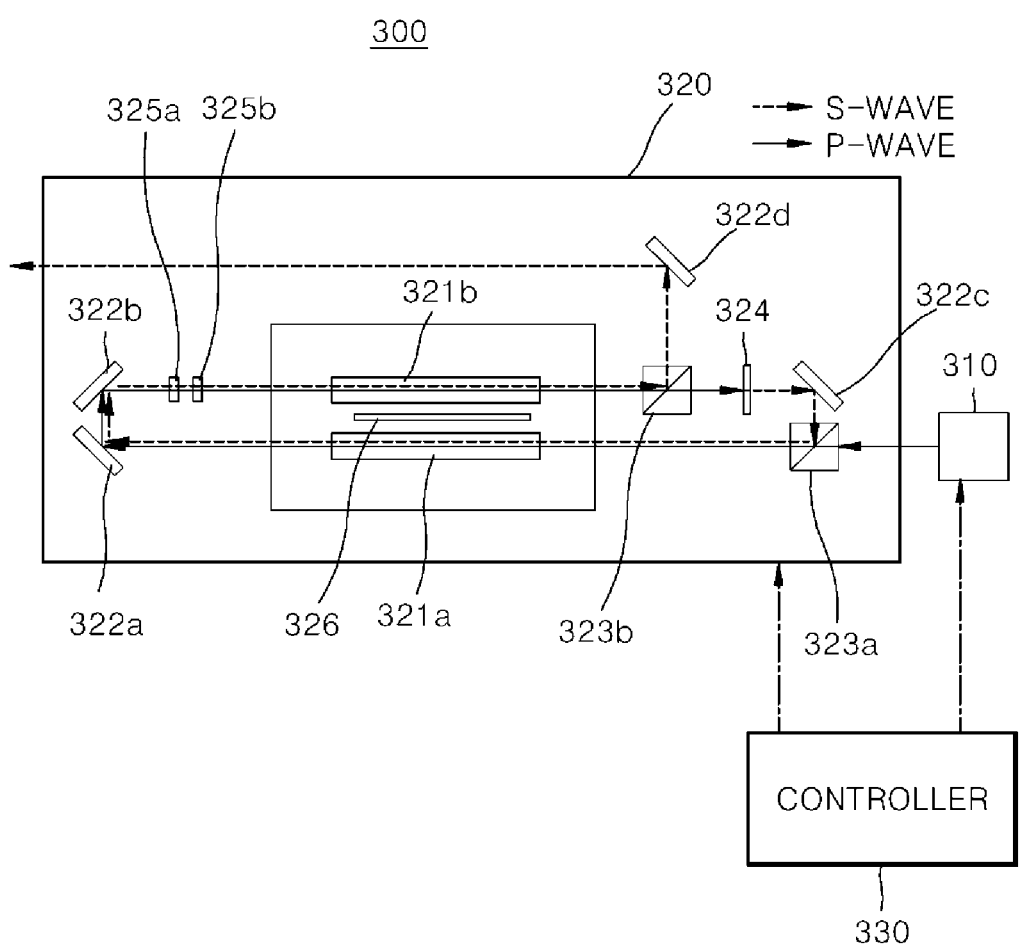
FIG. 4 is a schematic diagram of a laser device for skin treatment according to another embodiment of the present invention.

Referring to FIG. 4, a laser device for skin treatment 300 according to another embodiment of the present invention includes a laser generating unit 310, a laser amplifying unit 320, and a controller 330. Although not shown, the laser generating unit 310 may include a laser source generating unit (not shown) and a pulse width adjustment unit. The laser generating unit 310 and the controller 330 are similar to those of the laser device for skin treatment 100 of FIG. 1 and thus, a description thereof will be omitted.

The laser amplifying unit 320 includes a first beam splitter 323*a*, a first amplification medium 321*a*, a first mirror 322*a*, a second mirror 322*b*, a first lens 325*a*, a second lens 325*b*, a second amplification medium 321*b*, a first pumping lamp 325, a second beam splitter 323*b*, a first wave plate 324, a third mirror 322*c*, and a fourth mirror 322*d*. Although not shown, an SHG (not shown) as in FIG. 1 may be further included in the laser amplifying unit 320. The first beam splitter 323*a* transmits P-polarized light and reflects S-polarized light. Thus, the laser pulse supplied from the laser generating unit 310 is a P-wave as in the laser generating unit 310 shown in FIG. 1 and thus transmits the first beam splitter 323*a* as it is. Also, the first beam splitter 323*a* is arranged on the same axis as the proceeding direction of the laser source supplied from the laser generating unit 310. Of course, the arrangement of the first beam splitter 323*a* may be changed.

The first amplification medium 321*a* serves to amplify the laser source supplied from the laser generating unit 310. The first pumping lamp 326 illuminates the first amplification medium 321*a* so as to excite ions in the first amplification medium 321*a*. The first pumping lamp 326 is spaced apart from the first amplification medium 321*a*. The first amplification medium 321*a* is formed in a rod structure. The first amplification medium 321*a* is formed of Nd:YAG. However, in the present invention, the structure and shape of the first amplification medium 321*a* may be changed as much as possible.

Also, the first amplification medium 321*a* is arranged on the same axis as the first beam splitter 323*a*. Thus, the laser pulse that transmits the first beam splitter 323*a* is firsts amplified while passing through the first amplification medium 321*a*.

The first mirror 322*a* is arranged to face the first beam splitter 323*a* with the first amplification medium 321*a* therebetween. The first mirror 322*a* reflects the laser pulse passing through the first amplification medium 321*a* to change the path of the laser pulse.

The second mirror 322*b* reflects the laser pulse having the path changed by the first mirror 322*a* to change the path again. The second mirror 322*b* is arranged on one side of the first mirror 322*a*.

The second amplification medium 321*b* serves to second amplify the laser pulse reflected from the second mirror 322*b*. The second amplification medium 321*b* is spaced apart from the first amplification medium 321*a*. The first pumping lamp 326 illuminates the second amplification medium 321*b* so as to excite ions in the second amplification medium 321*b*. The first pumping lamp 326 is spaced apart from the second amplification medium 321*b*. The first amplification medium 321*b* is formed in a rod structure. Also, the first amplification medium 321*b* is formed of Nd:YAG. However, in the present invention, the structure and shape of the first amplification medium 321*b* may be changed as much as possible.

Also, the second amplification medium 321*b* is arranged on the same axis as the second mirror 322*b*. Thus, the laser pulse reflected from the second mirror 322*b* is second amplified while passing through the second amplification medium 321*b*.

The first lens 325*a* and the second lens 325*b* is arranged between the second mirror 322*b* and the second amplification medium 321*b*. The first lens 325*a* and the second lens 325*b* adjust the spatial size of the laser pulse reflected from the second mirror 322*b*.

The second beam splitter 323*b* is arranged to face the second mirror 322*b* with the second amplification medium 321*b* therebetween. Since the second amplified laser pulse is a P-wave, the second beam splitter 323*b* transmits the second amplified laser pulse.

The third mirror 322*c* reflects the laser pulse transmitting the second beam splitter 323*b* to change the path of the laser pulse. The third mirror 322*c* is arranged to face the second amplification medium 321*b* with the second beam splitter 323*b* therebetween.

The first wave plate 324 is arranged between the second beam splitter 323*b* and the third mirror 322*c*. The first wave plate 324 is formed as a half wave plate. Thus, the waveform of the laser pulse that passes through the first wave plate 324 is changed from the P-wave to the S-wave.

The third mirror 322*c* is arranged to face the second beam splitter 323*b* with the first wave plate 324 therebetween. Also, the third mirror 322*c* is arranged on one side of the first beam splitter 323*a*. The laser pulse having the path changed by being reflected from the third mirror 322*c* returns to the first beam splitter 323*a* and is reflected. The laser pulse reflected from the first beam splitter 323*a* is directed to the first amplification medium 321*a*.

The laser pulse that is third amplified while passing through the first amplification medium 321*a* is reflected from the first mirror 322*a*, and the path of the laser pulse is changed. The laser pulse having the path changed by being reflected from the first mirror 322*a* is reflected from the second mirror 322*b*, and the path of the laser pulse is changed, and the laser pulse is directed to the second amplification medium 321*b*.

The laser pulse that is fourth amplified while passing through the second amplification medium 321*b* is reflected by the second beam splitter 321*b*, and the path of the laser pulse is changed. Since the waveform of the laser pulse while passing through the first wave plate 324 has been changed to the S-wave, the laser pulse does not transmit the second beam splitter 323*b* but is reflected, and the path of the laser pulse is changed.

The fourth mirror 322*d* is arranged on one side of the second beam splitter 323*b*. The fourth mirror 322*d* is arranged on one side of the second beam splitter 323*b*. The fourth mirror 322*d* changes the path of the laser pulse reflected by the second beam splitter 323*b* and outputs the laser pulse.

The laser device for skin treatment 300 according to the present embodiment has an advantage of having a simpler structure than the laser device for skin treatment 200 of FIG. 3 and good amplification efficiency, because the number of amplification times is the same as four times compared to the laser device for skin treatment 200 of FIG. 3 and the number of wave plates is less than that of the laser device for skin treatment 200 of FIG. 2.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

By using the present invention, a laser device for skin treatment in which the width of a pulse generated by a laser generating unit can be conveniently adjusted and the pulse can be easily amplified by a laser amplifying unit, can be provided.

The invention claimed is:

1. A laser device for skin treatment, comprising:
a laser generating unit generating a pulse having an adjusted pulse width; and
a laser amplifying unit amplifying the pulse supplied from the laser generating unit,
wherein the laser amplifying unit comprises:
a first amplification medium for first amplifying the pulse supplied from the laser generating unit; and
a first mirror arranged to reflect the laser pulse first amplified while passing through the first amplification medium and to return the first amplified laser pulse in a direction of the first amplification medium;
a first beam splitter arranged to face the first mirror with the first amplification medium therebetween and to adjust a path of the pulse second amplified while returning to and passing through the first amplification medium;
a first wave plate arranged between the first mirror and the first beam splitter to change a polarization or phase of the passing pulse;
a second mirror transmitting the pulse having the path adjusted by the first beam splitter to a second amplification medium;
the second amplification medium spaced apart from the first amplification medium and for third amplifying the pulse supplied from the second mirror;
a first pumping lamp spaced apart from the first amplification medium and the second amplification medium and illuminating the first amplification medium and the second amplification medium;
a third mirror arranged to face the second mirror with the second amplification medium therebetween, to reflect the pulse third amplified while passing through the second amplification medium and to adjust a path of the third amplified pulse;
a fourth mirror transmitting the pulse having the path adjusted by the third mirror to a third amplification medium;
a third amplification medium for fourth amplifying the pulse supplied from the fourth mirror;
a fifth mirror arranged to face the fourth mirror with the third amplification medium therebetween, to reflect the pulse fourth amplified while passing through the third amplification medium and to adjust a path of the fourth amplified pulse;
a sixth mirror transmitting the pulse having the path adjusted by the fifth mirror to a fourth amplification medium;
a fourth amplification medium for fifth amplifying the pulse supplied from the sixth mirror;
a second pumping lamp spaced apart from the third amplification medium and the fourth amplification medium and illuminating the third amplification medium and the fourth amplification medium; and
a seventh mirror arranged to face the sixth mirror with the fourth amplification medium therebetween, to reflect the pulse passing through the fourth amplification medium and to adjust a path of the pulse, and
wherein the pulse supplied from the laser generating unit transmits the first beam splitter and is directed to the first amplification medium.

2. The laser device for skin treatment of claim 1, wherein the laser generating unit comprises:
a laser source generating unit; and
a pulse width adjustment unit adjusting energy and a pulse width of a laser source generated by the laser source generating unit to generate modulated laser sources having set energy and pulse widths.

3. The laser device for skin treatment of claim 2, wherein the pulse width adjustment unit sends out any one of a plurality of modulated laser sources or any one of laser sources generated by the laser source generating unit to the laser amplifying unit, alternately sends out any one of the plurality of modulated laser sources and the laser sources generated by the laser source generating unit to the laser amplifying unit, alternately sends out the plurality of modulated laser sources and the laser sources generated by the laser source generating unit to the laser amplifying unit, or alternately sends out the plurality of modulated laser sources to the laser amplifying unit.

4. The laser device for skin treatment of claim 1, further comprising a lens unit arranged between the third mirror and the fourth mirror and adjusting a size of the pulse reflected from the third mirror.

5. The laser device for skin treatment of claim 1, further comprising:
an eighth mirror reflecting the pulse having the path adjusted by the seventh mirror to adjust a path of the pulse and to output the pulse; and
a second harmonic generator (SHG) changing a wavelength of the pulse output by the eighth mirror.

6. A laser device for skin treatment, comprising:
a laser generating unit generating a pulse having an adjusted pulse width; and
a laser amplifying unit amplifying the pulse supplied from the laser generating unit,
wherein the laser amplifying unit comprises:
a first amplification medium for first amplifying the pulse supplied from the laser generating unit;
a first mirror arranged to reflect the laser pulse first amplified while passing through the first amplification medium and to return the first amplified laser pulse in a direction of the first amplification medium;
a first beam splitter arranged to face the first mirror with the first amplification medium therebetween and to adjust a path of the pulse second amplified while returning to and passing through the first amplification medium;
a first wave plate arranged between the first mirror and the first beam splitter to change a polarization or phase of the passing pulse;
a second mirror transmitting the pulse having the path adjusted by the first beam splitter to a second amplification medium;
the second amplification medium spaced apart from the first amplification medium and for third amplifying the pulse supplied from the second mirror;
a first pumping lamp spaced apart from the first amplification medium and the second amplification medium and illuminating the first amplification medium and the second amplification medium;
a third mirror arranged to reflect the pulse third amplified while passing through the second amplification medium and to return the third amplified pulse in a direction of the second amplification medium;
a second beam splitter arranged to face the third mirror with the second amplification medium therebetween and to adjust a path of the pulse fourth amplified while returning to and passing through the second amplification medium;
a third wave plate arranged between the third mirror and the second beam splitter to change a polarization or phase of the passing pulse; and
a second wave plate in which the pulse reflected from the second mirror is supplied to the second amplification medium through the second beam splitter and which is arranged between the second mirror and the second beam splitter and changing a polarization or phase of the pulse reflected from the second mirror and directed to the second beam splitter, and
wherein the pulse supplied from the laser generating unit transmits the first beam splitter and is directed to the first amplification medium.

7. The laser device for skin treatment of claim 6, further comprising a lens unit arranged between the second beam splitter and the second wave plate and adjusting a size of the pulse having a polarization or phase changed by the second wave plate.

8. The laser device for skin treatment of claim 6, further comprising:
a fourth mirror reflecting the pulse having the path adjusted by the second beam splitter to output the pulse to the laser amplifying unit; and
a second harmonic generator (SHG) changing a wavelength of the pulse output by the fourth mirror.

9. A laser device for skin treatment, comprising:
a laser generating unit generating a pulse having an adjusted pulse width; and
a laser amplifying unit amplifying the pulse supplied from the laser generating unit,
wherein the laser amplifying unit comprises:
a first amplification medium for first amplifying the pulse supplied from the laser generating unit;
a first mirror adjusting a path of the pulse first amplified while passing through the first amplification medium;
a second mirror transmitting the pulse having the path adjusted by the first mirror to a second amplification medium;
the second amplification medium spaced apart from the first amplification medium and for second amplifying the pulse supplied from the second mirror;
a first pumping lamp spaced apart from the first amplification medium and the second amplification medium and illuminating the first amplification medium and the second amplification medium;
a second beam splitter allowing the second amplified pulse by the second amplification medium to pass;
a third mirror arranged to face the second amplification medium with the second beam splitter therebetween, to reflect the pulse second amplified while passing through the second amplification medium and passing through the second beam splitter and to adjust a path of the pulse;
a first wave plate arranged between the third mirror and the second beam splitter to change a polarization or phase of the pulse passing through the second beam splitter and directed to the third mirror;
a first beam splitter arranged to face the first mirror with the first amplification medium therebetween, to reflect the pulse having the path adjusted by the third mirror and to adjust a path of the pulse,
wherein the pulse having the path adjusted by the first beam splitter is third amplified while passing the first amplification medium, the third amplified pulse is directed to the second mirror while the path of the third amplified pulse is adjusted by the first mirror, the pulse having the path adjusted by the second mirror is directed to the second amplification medium, and the fourth amplified pulse while passing through the second amplification medium is sent out while the path of the fourth amplified pulse is adjusted by the second beam splitter, and
the pulse supplied from the laser generating unit transmits the first beam splitter and is directed to the first amplification medium.

10. The laser device for skin treatment of claim 9, further comprising a lens unit arranged between the second mirror and the second beam splitter and adjusting a size of the pulse having the path adjusted by the second mirror.

11. The laser device for skin treatment of claim 9, further comprising:
a fourth mirror reflecting the pulse having the path adjusted by the second beam splitter to output the pulse to the laser amplifying unit; and
a second harmonic generator (SHG) changing a wavelength of the pulse output by the fourth mirror.

* * * * *